(12) United States Patent
Lin

(10) Patent No.: US 6,752,627 B2
(45) Date of Patent: Jun. 22, 2004

(54) LIGHT EMITTING TOOTH BRUSH HAVING WHITENING AND STERILIZING EFFECTS

(75) Inventor: Ray-Ming Lin, Shinjuang (TW)

(73) Assignee: Chang Gung University, Tao-Yuan (TW)

(*) Notice: Subject to any disclaimer, the term of this patent is extended or adjusted under 35 U.S.C. 154(b) by 82 days.

(21) Appl. No.: 10/243,476

(22) Filed: Sep. 13, 2002

(65) Prior Publication Data

US 2004/0053190 A1 Mar. 18, 2004

(51) Int. Cl.[7] .................... A61C 1/00; A46B 15/00; F21V 33/00
(52) U.S. Cl. .................... 433/29; 15/167.1; 362/109
(58) Field of Search .................... 433/29, 31; 15/167.1; 362/109, 119, 120

(56) References Cited

U.S. PATENT DOCUMENTS

| | | | | |
|---|---|---|---|---|
| 3,261,978 A | * | 7/1966 | Brenman | |
| 4,779,173 A | * | 10/1988 | Carr et al. | 362/109 |
| 5,030,090 A | * | 7/1991 | Maeda et al. | 433/29 |
| 5,306,143 A | * | 4/1994 | Levy | 433/29 |
| 5,339,479 A | * | 8/1994 | Lyman | 15/105 |
| 5,658,148 A | * | 8/1997 | Neuberger et al. | 433/215 |
| 5,813,855 A | * | 9/1998 | Crisio, Jr. | 433/29 |
| 6,026,828 A | * | 2/2000 | Altshuler | 132/311 |
| 6,029,304 A | * | 2/2000 | Hulke et al. | 15/105 |
| 6,106,294 A | * | 8/2000 | Daniel | 433/216 |
| 6,290,496 B1 | * | 9/2001 | Azar et al. | 433/29 |
| 6,468,076 B2 | * | 10/2002 | Kawamura | 433/29 |
| 6,606,755 B1 | * | 8/2003 | Robinson et al. | 15/105 |
| 6,616,451 B1 | * | 9/2003 | Rizolu et al. | 433/215 |
| 6,623,272 B2 | * | 9/2003 | Clemans | 433/215 |

* cited by examiner

Primary Examiner—Cary E. O'Connor
(74) Attorney, Agent, or Firm—Alan D. Kamrath; Nikolai & Mersereau, P.A.

(57) ABSTRACT

A light emitting tooth brush having whitening and sterilizing effects includes a handle having one end provided with a light permeable brush head, a control switch mounted in the handle, and a circuit board mounted in the brush head. The circuit board is electrically connected to the control switch, and is provided with a light emitting member which may emit optical waves having a specified wavelength through the light permeable brush head. Thus, the light emitting tooth brush may achieve the sterilizing effect and may achieve the effect of cleaning and whitening the user's teeth.

8 Claims, 4 Drawing Sheets

LIGHT EMITTING TOOTH BRUSH HAVING WHITENING AND STERILIZING EFFECTS

BACKGROUND OF THE INVENTION

1. Field of the Invention

The present invention relates to a light emitting tooth brush having whitening and sterilizing effects, and more particularly to a light emitting tooth brush that may achieve the sterilizing effect and may achieve the effect of cleaning and whitening the user's teeth.

2. Description of the Related Art

A conventional tooth brush may co-operate with the tooth paste to brush the user's teeth. However, the conventional tooth brush cannot achieve the sterilizing effect and cannot achieve the effect of whitening the user's teeth, thereby decreasing the utility and versatility of the conventional tooth brush.

SUMMARY OF THE INVENTION

The present invention has arisen to mitigate and/or obviate the disadvantage of the conventional tooth brush.

The primary objective of the present invention is to provide a light emitting tooth brush having whitening and sterilizing effects, wherein the light emitting member of the circuit board may emit ultraviolet rays with shorter wavelengths (with a greater energy), thereby achieving a sterilizing effect.

Another objective of the present invention is to provide a light emitting tooth brush having whitening and sterilizing effects, wherein the light emitting tooth brush may promote the optical chemical reaction between the tooth paste and the surface of the user's teeth, so that the light emitting tooth brush may clean and whiten the surface of the user's teeth efficiently, thereby achieving the effect of cleaning and whitening the user's teeth.

In accordance with the present invention, there is provided a light emitting tooth brush having whitening and sterilizing effects, comprising a handle having one end provided with a light permeable brush head, a control switch mounted in the handle, and a circuit board mounted in the brush head, wherein: the circuit board is electrically connected to the control switch, and is provided with a light emitting member which may emit optical waves having a specified wavelength through the light permeable brush head.

Further benefits and advantages of the present invention will become apparent after a careful reading of the detailed description with appropriate reference to the accompanying drawings.

DETAILED DESCRIPTION OF THE INVENTION

Figure 1:
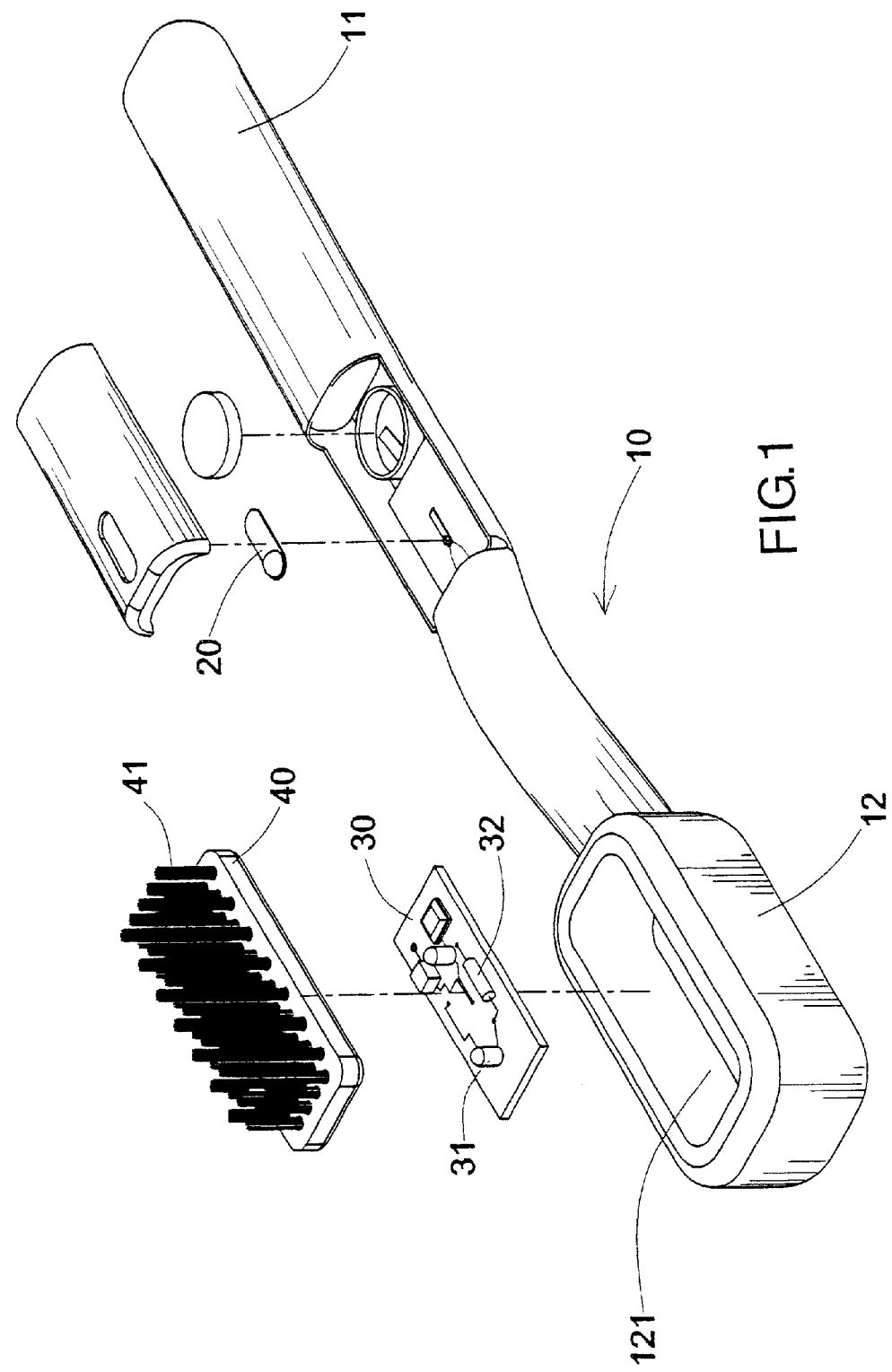
FIG. 1 is an exploded perspective view of a light emitting tooth brush having whitening and sterilizing effects in accordance with a preferred embodiment of the present invention.
Figure 2:
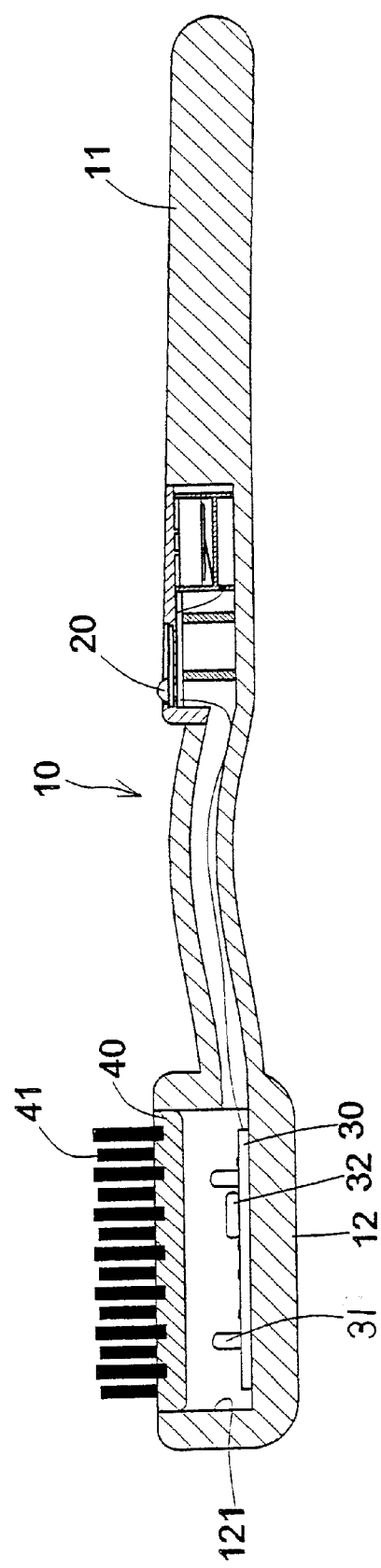
FIG. 2 is a side plan cross-sectional assembly view of the light emitting tooth brush having whitening and sterilizing effects as shown in FIG. 1.
Figure 3:
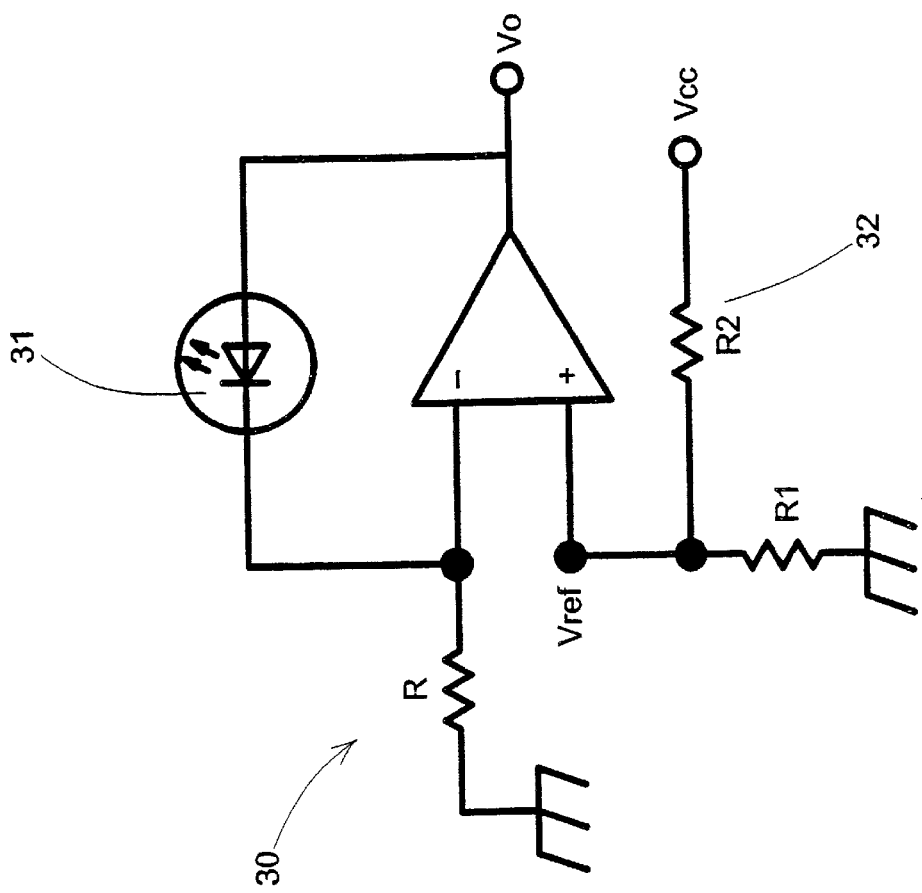
FIG. 3 is a schematic circuit diagram of the circuit board of the light emitting tooth brush having whitening and sterilizing effects in accordance with a preferred embodiment of the present invention.

Referring to the drawings and initially to FIGS. 1–3, a light emitting tooth brush 10 having whitening and sterilizing effects in accordance with a preferred embodiment of the present invention comprises a handle 11 having one end provided with a light permeable brush head 12, a control switch 20 mounted in the handle 11, a circuit board 30 mounted in the brush head 12, and a support plate 40 mounted on a top of the brush head 12 to closely seal the brush head 12, so that the circuit board 30 is closely mounted in the brush head 12 by the support plate 40.

The brush head 12 is formed with a receiving space 121 for receiving the circuit board 30, and the support plate 40 is mounted on a top of the receiving space 121 of the brush head 12 to closely seal the circuit board 30 in the brush head 12.

The circuit board 30 is electrically connected to the control switch 20, and is provided with a light emitting member 31 and a plurality of resistors 32. The light emitting member 31 of the circuit board 30 may emit ultraviolet rays, viewable rays, such as red rays and violet rays, and may emit infrared rays. Preferably, the light emitting member 31 of the circuit board 30 is a light emitting diode or a laser diode. The resistors 32 of the circuit board 30 may be used to adjust the light emitting strength of the light emitting member 31 of the circuit board 30.

The support plate 40 is provided with multiple brushes 41.

Figure 4:
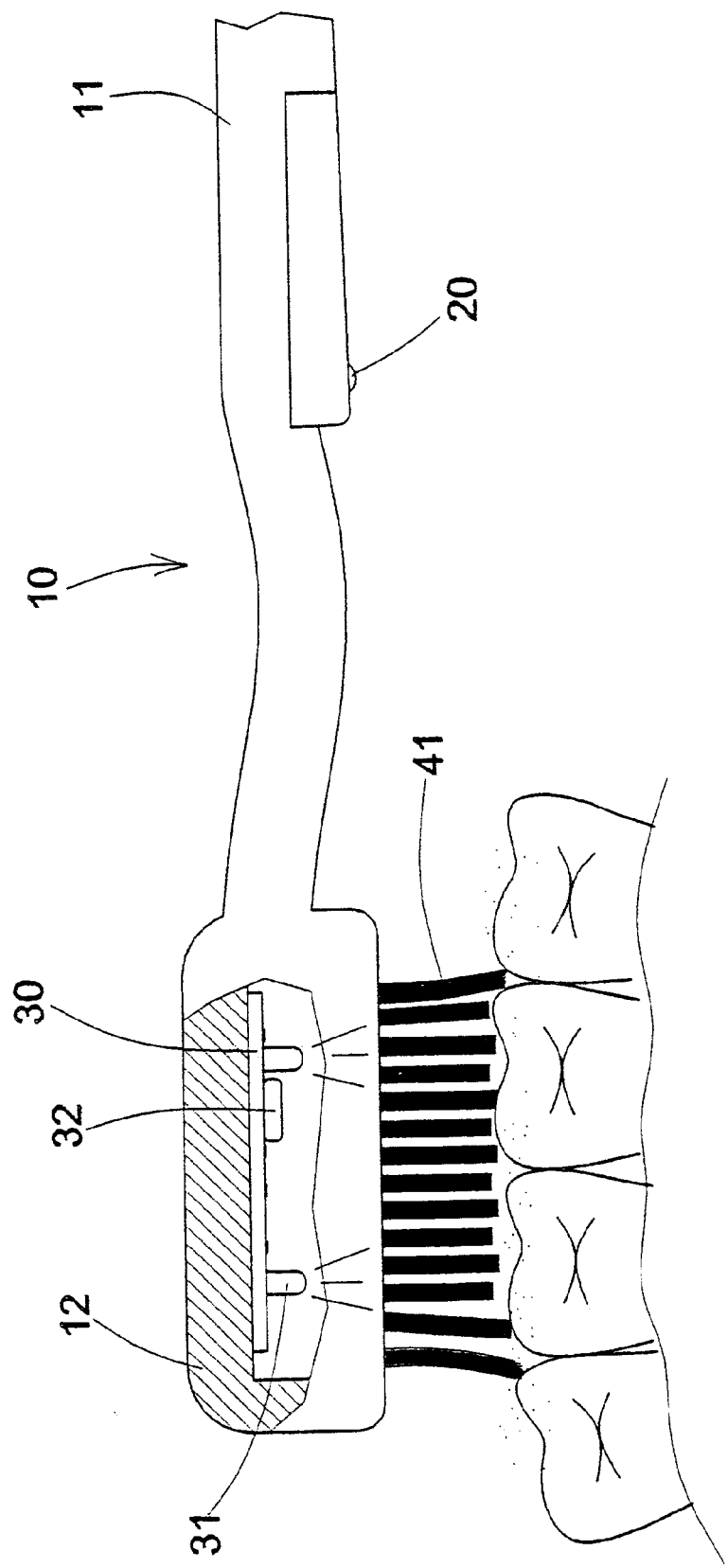
FIG. 4 is a schematic operational view of the light emitting tooth brush having whitening and sterilizing effects as shown in FIG. 2 in use.

In practice, referring to FIG. 4 with reference to FIGS. 1–3, the light emitting member 31 of the circuit board 30 may emit ultraviolet rays with shorter wavelengths (with a greater energy), thereby achieving a sterilizing effect. Thus, when the user is using the light emitting tooth brush 10 to brush his teeth, the control switch 20 may be started to provide an electric power to the circuit board 30, so that the light emitting member 31 of the circuit board 30 may emit ultraviolet rays which may pass through the light permeable brush head 12 into the user's mouth, thereby achieving a sterilizing effect. In addition, the light emitting member 31 of the circuit board 30 may emit ultraviolet rays which may promote the optical chemical reaction between the tooth paste and the surface of the user's teeth, thereby decreasing the activation energy of the chemical reaction or changing the reaction path, so as to accelerate the chemical reaction of the surface of the user's teeth, so that the dregs or spots attached on the surface of the user's teeth may be removed.

Thus, the light emitting tooth brush 10 may promote the optical chemical reaction between the tooth paste and the surface of the user's teeth, so that the light emitting tooth brush 10 may clean and whiten the surface of the user's teeth efficiently, thereby achieving the effect of cleaning and whitening the user's teeth.

Accordingly, the light emitting tooth brush 10 in accordance with the present invention may achieve the sterilizing effect and may achieve the effect of cleaning and whitening the user's teeth.

In addition, referring to FIGS. 3 and 4, the control switch 20 may be adjusted to change the values of the resistor 32 of the circuit board 30, so as to control the values of the current passing through the light emitting member 31 of the circuit board 30, thereby controlling the light emitting strength of the light emitting member 31 of the circuit board 30, so as to achieve different ranges of sterilizing and whitening effects.

Although the invention has been explained in relation to its preferred embodiment as mentioned above, it is to be understood that many other possible modifications and variations can be made without departing from the scope of the present invention. It is, therefore, contemplated that the appended claim or claims will cover such modifications and variations that fall within the true scope of the invention.

What is claimed is:

1. A light emitting tooth brush having whitening and sterilizing effects, comprising a handle having one end provided with a light permeable brush head, a control switch mounted in the handle, and a circuit board mounted in the brush head, wherein: the circuit board is electrically connected to the control switch, and is provided with a light emitting member which may emit optical waves having a specified wavelength through the light permeable brush head.

2. The light emitting tooth brush having whitening and sterilizing effects in accordance with claim 1, further comprising a support plate mounted on a top of the brush head to closely seal the brush head, so that the circuit board is closely mounted in the brush head by the support plate.

3. The light emitting tooth brush having whitening and sterilizing effects in accordance with claim 2, wherein the brush head is formed with a receiving space for receiving the circuit board, and the support plate is mounted on a top of the receiving space of the brush head to closely seal the circuit board in the brush head.

4. The light emitting tooth brush having whitening and sterilizing effects in accordance with claim 2, wherein the support plate is provided with multiple brushes.

5. The light emitting tooth brush having whitening and sterilizing effects in accordance with claim 1, wherein the circuit board is provided with and a plurality of resistors to adjust a light emitting strength of the light emitting member of the circuit board.

6. The light emitting tooth brush having whitening and sterilizing effects in accordance with claim 1, wherein the light emitting member of the circuit board may emit ultraviolet rays, viewable rays, and may emit infrared rays.

7. The light emitting tooth brush having whitening and sterilizing effects in accordance with claim 1, wherein the light emitting member of the circuit board is a light emitting diode.

8. The light emitting tooth brush having whitening and sterilizing effects in accordance with claim 1, wherein the light emitting member of the circuit board is a laser diode.

* * * * *